(12) United States Patent  
Schafer et al.

(10) Patent No.: US 9,333,005 B2  
(45) Date of Patent: May 10, 2016

(54) ULTRASONIC PROBE FOR TREATING CELLULITE

(71) Applicant: Sound Surgical Technologies, LLC, Louisville, CO (US)

(72) Inventors: Mark E. Schafer, Ambler, PA (US); Dave Wesley, Lyons, CO (US); Adnan Merchant, Fremont, CA (US)

(73) Assignee: SOUND SURGICAL TECHNOLOGIES LLC, Louisville, CO (US)

( * ) Notice: Subject to any disclaimer, the term of this patent is extended or adjusted under 35 U.S.C. 154(b) by 363 days.

(21) Appl. No.: 13/654,216

(22) Filed: Oct. 17, 2012

(65) Prior Publication Data

US 2013/0096596 A1  Apr. 18, 2013

Related U.S. Application Data

(60) Provisional application No. 61/548,190, filed on Oct. 17, 2011, provisional application No. 61/563,366, filed on Nov. 23, 2011.

(51) Int. Cl.  
*A61B 17/32* (2006.01)  
*A61B 17/30* (2006.01)  
*A61N 7/00* (2006.01)

(52) U.S. Cl.  
CPC ... *A61B 17/320068* (2013.01); *A61B 2017/306* (2013.01); *A61B 2017/320072* (2013.01); *A61M 2202/08* (2013.01); *A61N 2007/0008* (2013.01)

(58) Field of Classification Search  
CPC ............... A61B 17/320068; A61B 2017/306; A61B 2017/320072; A61B 17/22004; A61B 2017/320076; A61B 2017/32008; A61B 2017/320084; A61B 2017/320088; A61B 2017/320096; A61B 17/22012; A61F 9/00745; A61F 9/00754; A61C 3/03; A61N 2007/0008  
USPC ............ 606/167, 169, 170, 171, 175; 604/22, 604/35  
See application file for complete search history.

(56) References Cited

U.S. PATENT DOCUMENTS 5,123,903 A * 6/1992 Quaid et al. .................... 604/22  
5,205,817 A * 4/1993 Idemoto et al. ................. 604/22  
(Continued)

FOREIGN PATENT DOCUMENTS

CN  101190138 A  6/2008

OTHER PUBLICATIONS

The International Bureau of WIPO, International Preliminary Report on Patentability issued in International application No. PCT/US2012/060532 dated Apr. 22, 2014.  
(Continued)

*Primary Examiner* — Ryan J Severson  
*Assistant Examiner* — Christian Knauss  
(74) *Attorney, Agent, or Firm* — Thopmson Hine LLP; Toan Vo

(57) ABSTRACT

An ultrasonic probe transmits ultrasonic energy along a shaft from a proximate end to a distal end. The ultrasonic probe includes at least one notch on its distal end. Fibrous tissue, such as septa that connect skin layers to muscle layers of animal tissue, can be positioned within the notch so that it is in contact with at least a portion of the distal end of the ultrasonic probe. The ultrasonic energy conducted through the ultrasonic probe to the distal end will sever the fibrous tissue in the notch. The ultrasonic probe is also designed, in embodiments, to fragment or emulsify adipose tissue, as part of an ultrasonic assisted lipoplasty (UAL) procedure.

7 Claims, 12 Drawing Sheets

(56) References Cited

U.S. PATENT DOCUMENTS

| | | | |
|---|---|---|---|
| 5,304,115 A * | 4/1994 | Pflueger et al. | 604/22 |
| 5,379,773 A * | 1/1995 | Hornsby | 600/466 |
| 5,527,273 A | 6/1996 | Manna et al. | |
| 5,674,235 A * | 10/1997 | Parisi | 606/169 |
| 5,879,364 A * | 3/1999 | Bromfield et al. | 606/169 |
| 6,224,565 B1 | 5/2001 | Cimino | |
| 6,241,703 B1 * | 6/2001 | Levin et al. | 604/22 |
| 6,328,751 B1 * | 12/2001 | Beaupre | 606/169 |
| 6,368,299 B1 * | 4/2002 | Cimino | A61B 17/22012 601/2 |
| 6,379,326 B1 | 4/2002 | Cimino | |
| 6,391,042 B1 | 5/2002 | Cimino | |
| 6,423,082 B1 * | 7/2002 | Houser et al. | 606/169 |
| 6,436,115 B1 * | 8/2002 | Beaupre | 606/169 |
| 6,561,983 B2 * | 5/2003 | Cronin et al. | 600/461 |
| 6,723,110 B2 * | 4/2004 | Timm et al. | 606/169 |
| 2002/0029054 A1 * | 3/2002 | Rabiner et al. | 606/169 |
| 2002/0156492 A1 * | 10/2002 | Timm et al. | 606/169 |
| 2003/0023257 A1 * | 1/2003 | Ishikawa et al. | 606/169 |
| 2003/0130655 A1 | 7/2003 | Woloszko et al. | |
| 2003/0158566 A1 * | 8/2003 | Brett | 606/167 |
| 2003/0204199 A1 * | 10/2003 | Novak et al. | 606/169 |
| 2004/0267211 A1 * | 12/2004 | Akahoshi | 604/264 |
| 2005/0037316 A1 * | 2/2005 | Sholder | 433/119 |
| 2005/0096554 A1 | 5/2005 | Dudik et al. | |
| 2005/0177117 A1 * | 8/2005 | Crocker et al. | 604/272 |
| 2005/0187513 A1 * | 8/2005 | Rabiner et al. | 604/22 |
| 2006/0211943 A1 * | 9/2006 | Beaupre | 600/471 |
| 2006/0235305 A1 * | 10/2006 | Cotter et al. | 600/459 |
| 2008/0132927 A1 | 6/2008 | Sakai | |
| 2008/0188835 A1 | 8/2008 | Hennings et al. | |
| 2008/0194999 A1 * | 8/2008 | Yamaha et al. | 601/2 |
| 2010/0168741 A1 * | 7/2010 | Sanai | A61B 17/320068 606/42 |
| 2010/0204721 A1 * | 8/2010 | Young et al. | 606/169 |
| 2010/0228182 A1 | 9/2010 | Clark, III et al. | |

OTHER PUBLICATIONS

Heo, Joo Hyung; ISA/KR, International Search Report issued in PCT/US2012/060532 dated Feb. 26, 2013.

Chinese Patent Office, Office Action issued in corresponding Application No. 2012800609199 dated Dec. 3, 2015.

\* cited by examiner

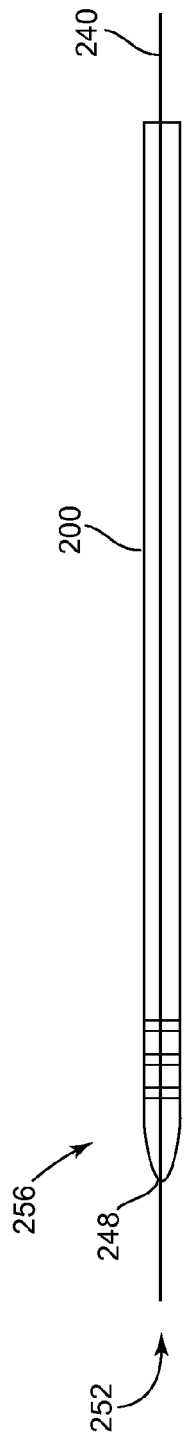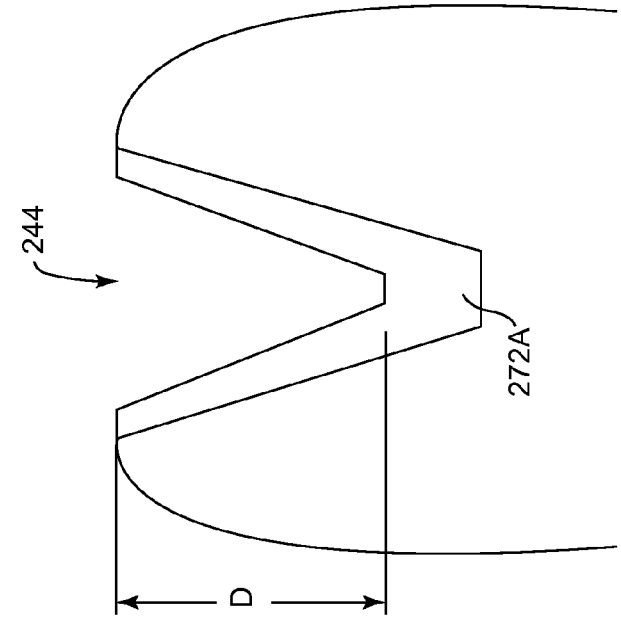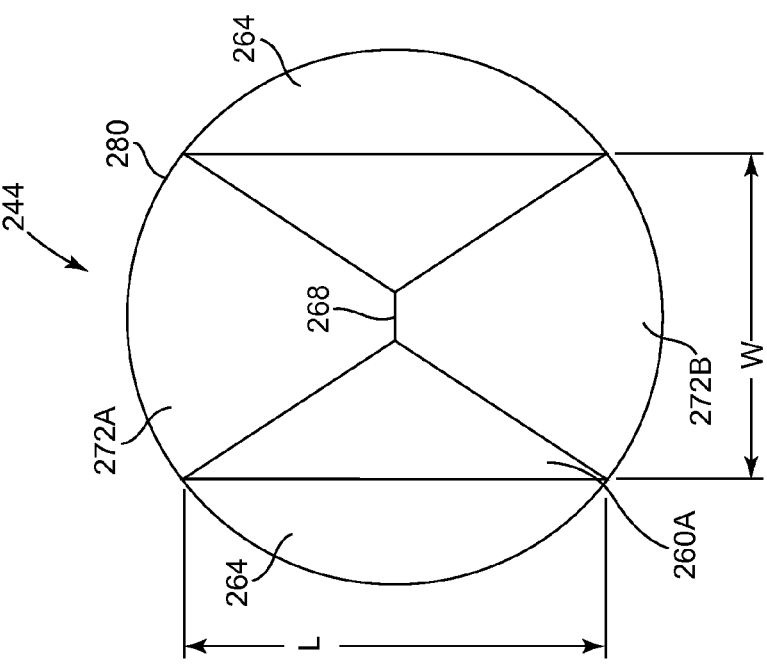

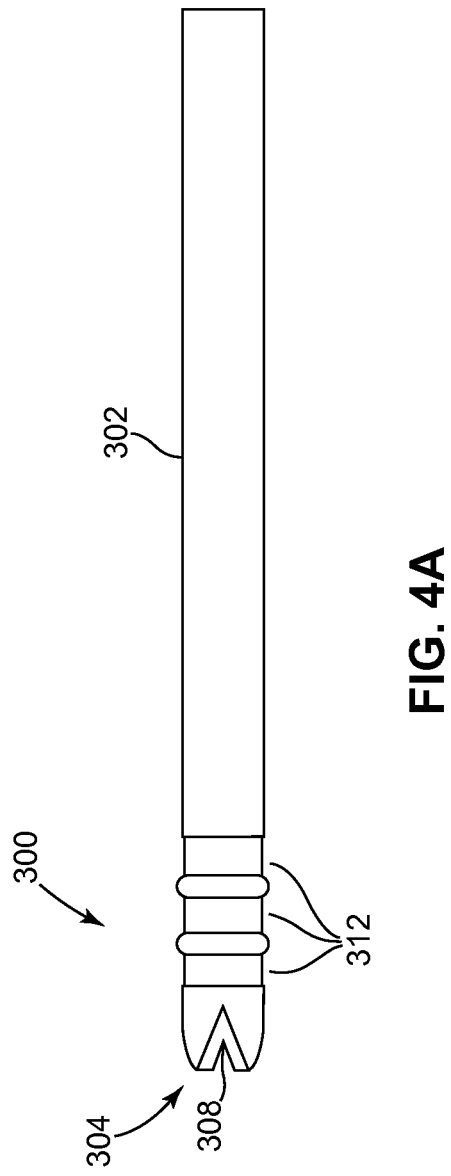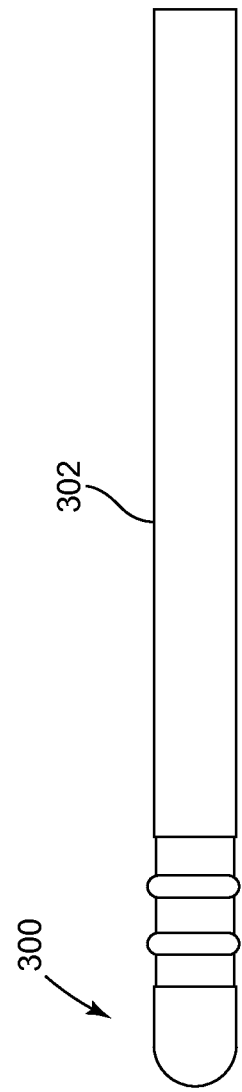

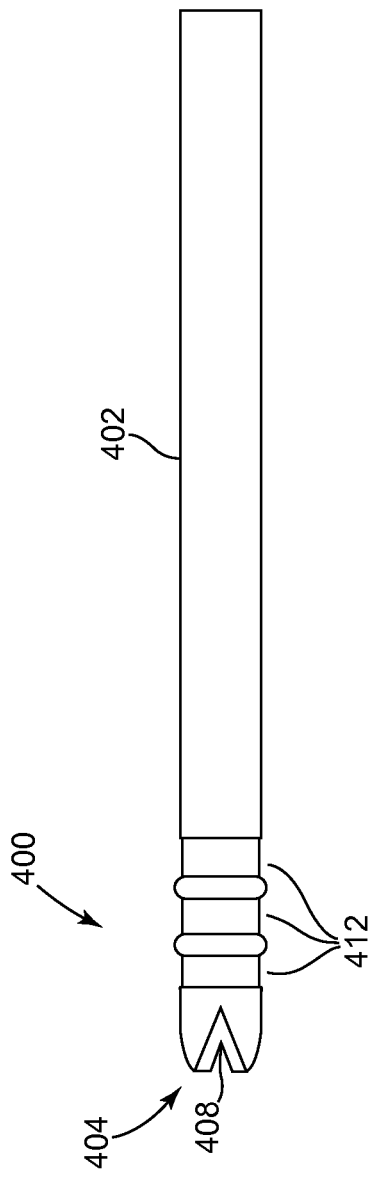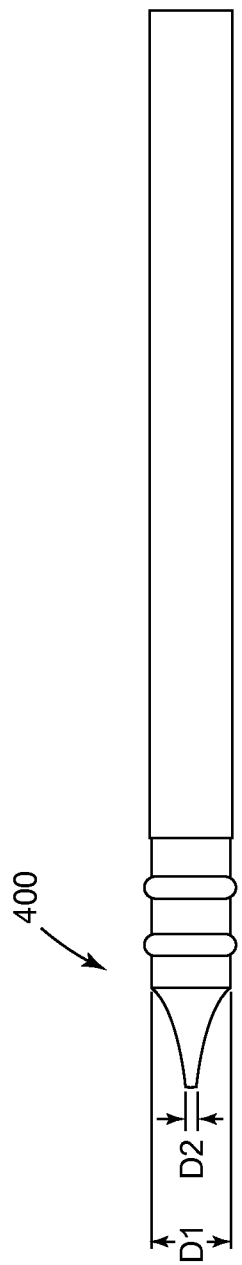

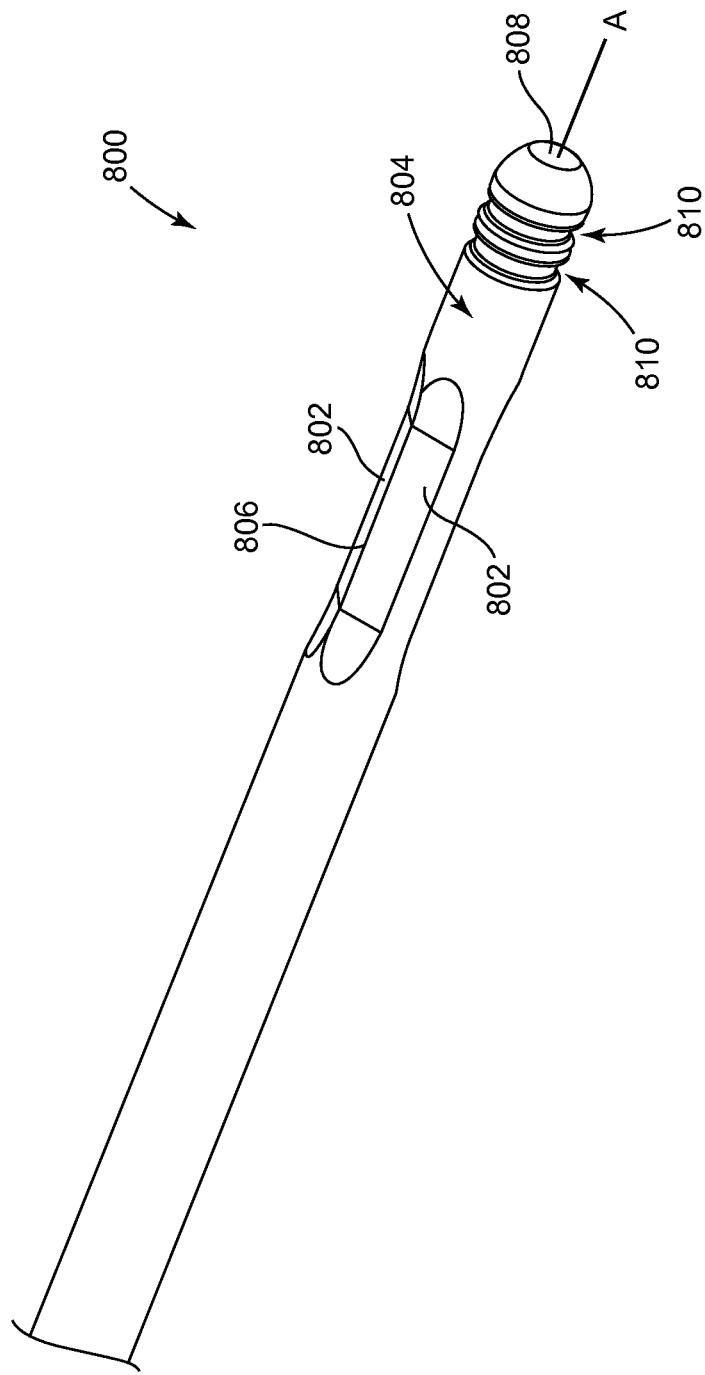

ULTRASONIC PROBE FOR TREATING CELLULITE

CROSS-REFERENCE TO RELATED APPLICATIONS

This application claims priority to and the benefit of U.S. Provisional Patent Application Ser. No. 61/548,190, filed Oct. 17, 2011, entitled "Ultrasonic Probe for Treating Cellulite"; and U.S. Provisional Patent Application Ser. No. 61/563,366, filed Nov. 23, 2011, entitled "Ultrasonic Probe for Treating Cellulite"; the disclosures of which are hereby incorporated by reference herein in their entireties.

FIELD

This technology relates to the field of ultrasonic devices and the application of ultrasonic energy in medicine. In particular, it relates to application of ultrasonic energy to sever fibrous tissue in an animal patient, e.g., human patient, and disassociate adipose tissue in the patient.

BACKGROUND

The term "cellulite" refers to the dimpled appearance of the skin that some people have on their bodies, commonly on hips, thighs, and buttocks. Cellulite is believed to be caused by cords of connective, fibrous tissue, referred to as "septa," which connect the skin to underlying muscle tissue. When fat cells, i.e., adipocytes, multiply and/or enlarge, they push up against the skin, which is being pulled down by the septa. This creates an uneven surface, e.g., dimpling, referred to as cellulite.

Cellulite is not a dangerous condition but many people find cellulite unsightly, and prefer their skin to have a smooth appearance. A number of different techniques have been developed to treat cellulite, each with varying results. Some techniques commonly involve treating the surface of the skin with one or more of mechanical energy (e.g., message), heat, pressure, light, radio frequencies, ultrasonic energy, chemical treatments and other sources of energy. These techniques attempt to shrink or move the fat cells that are pushing up against the skin to lessen the dimpled appearance of the skin.

Recently, some approaches have been developed for treating cellulite by cutting the septa, which allows the portion of skin previously pulled down by the septa to move with the increased volume of fat cells. This is believed to reduce the dimpling on the outer surface of the skin. These techniques however require that a surgeon apply enough force to a cutting instrument, such as a cannula or narrow scalpel, to physically cut through the fibrous tissue of the septa. In some instances, significant force must be applied by the surgeon. When the septa is suddenly cut, the applied force can thrust the cutting instrument forward or sideways into the patient (depending upon the septa was cut with the front surface of the canula or the side surface of the narrow scalpel), potentially resulting in undesirable contact of the cutting instrument with other tissues.

It is with respect to these and other considerations that embodiments of the present technology have been made. Also, although relatively specific problems have been discussed, it should be understood that embodiments of the present technology should not be limited to solving the specific problems identified in the background.

SUMMARY

This summary is provided to introduce a selection of concepts in a simplified form that are further described below in the Detail Description section. This summary is not intended to be used as an aid in determining the scope of the claimed subject matter.

Described are embodiments directed to an ultrasonic probe that can be used to treat cellulite. In embodiments, the present technology includes an ultrasonic probe that transmits ultrasonic energy along a shaft from a proximate end to a distal end. The ultrasonic probe includes at least one notch at its distal end. Fibrous tissue, such as septa that connect skin layers to muscle layers, can be positioned within the notch so that it is in contact with a cutting surface within the notch. The ultrasonic energy conducted through the ultrasonic probe to the cutting surface will sever the fibrous tissue in the notch. In another embodiment, the sides of the canula are designed to present cutting surfaces. In some embodiments, the ultrasonic probe is not only used to sever fibrous tissue, but is also designed to fragment or emulsify adipose tissue, as part of an ultrasonic assisted lipoplasty (UAL) procedure.

In one aspect, the technology relates to an ultrasonic probe for conducting ultrasonic energy to a surgical site for use in severing fibrous tissue and fragmenting adipose tissue, the ultrasonic probe including: proximate end configured to connect to an ultrasonic driver assembly that generates the ultrasonic energy; a shaft for conducting the ultrasonic energy from the proximate end to a distal end; and a cutting surface located proximate the distal end, wherein the cutting surface is adapted to contact fibrous tissue when the fibrous tissue is positioned in contact with the cutting surface. In an embodiment, the probe includes a notch located at the distal end of the ultrasonic probe, wherein the notch includes the cutting surface. In another embodiment, the shaft includes an outer surface, wherein the outer surface at least partially defines the cutting surface. In yet another embodiment, the outer surface defines a substantially rounded profile and the cutting surface defines a substantially straight profile. In still another embodiment, the cutting surface includes a plurality of cutting surfaces located symmetrically on the outer surface.

In another embodiment of the above aspect, the probe includes one or more grooves near the distal end, the grooves substantially circumscribing the shaft to reduce the tissue contact surface area along and about the sides of the distal end and providing additional tissue fragmenting surface area at the distal end. In another embodiment, the fibrous tissue includes septa underneath cellulite. In yet another embodiment a centerpoint of the cutting surface is located a predetermined distance from the distal end of the ultrasonic probe. In still another embodiment, the predetermined distance corresponds to an antinode of an ultrasonic longitudinal vibration pattern produced by the delivery of ultrasonic energy to the distal end of the ultrasonic probe. In another embodiment, a probe body cross section includes a probe body cross-sectional area, and wherein a cutting area cross section includes a cutting area cross-sectional area, wherein the cutting area cross-sectional area is about 95% to about 80% of the probe body cross-sectional area. In another embodiment, the cutting area cross-sectional area is about 80% of the probe body cross-sectional area.

In another aspect, the technology relates to a method of severing fibrous tissue, the method including: positioning the fibrous tissue proximate a cutting surface located proximate a distal end of an ultrasonic probe; and delivering ultrasonic energy to the distal end of the ultrasonic probe to sever the fibrous tissue in contact with the cutting surface. In an embodiment, the ultrasonic probe further includes a notch located at the distal end of the ultrasonic probe, wherein the notch includes the cutting surface, and wherein the method further includes positioning the fibrous tissue within the notch so as to contact the fibrous tissue. In another embodiment, a centerpoint of the cutting surface is located a predetermined distance from the distal end of the ultrasonic probe. In yet another embodiment, the predetermined distance corresponds to an antinode of an ultrasonic longitudinal vibration pattern produced by the delivery of ultrasonic energy to the distal end of the ultrasonic probe. In still another embodiment, the fibrous tissue includes septa underneath a skin layer, wherein an outside surface of the skin has cellulite. In another embodiment, the method includes pulling the skin layer away from an anatomical layer in order to identify septa to be severed.

In another aspect, the technology relates to an ultrasonic probe for conducting ultrasonic energy to a surgical site for use in severing fibrous tissue and fragmenting adipose tissue, the ultrasonic probe including: a probe body defining two cutting edges, wherein the at least two cutting edges are located substantially symmetrically about an outer circumference of the probe body, and wherein the probe body defines a plurality of substantially circumferential grooves about an outer surface of the probe body. In an embodiment, the plurality of circumferential grooves are located proximate a tip of the probe body. In another embodiment, the two cutting edges are located distal from the tip of the probe body.

BRIEF DESCRIPTION OF THE DRAWINGS

Non-limiting and non-exhaustive embodiments are described with reference to the following figures.

FIG. 3A illustrates a front view of an ultrasonic probe consistent with a first embodiment of the present technology.

FIG. 3B illustrates a top view of the embodiment shown in FIG. 3A.

FIG. 3C illustrates a side view of the embodiment shown in FIGS. 3A and 3B.

FIG. 4A illustrates a top view of a distal end of an ultrasonic probe consistent with a first embodiment of the present technology.

FIG. 4B illustrates a side view of the embodiment shown in FIG. 4A.

FIG. 5A illustrates a top view of a distal end of an ultrasonic probe consistent with a second embodiment of the present technology.

FIG. 5B illustrates a side view of the embodiment shown in FIG. 5A.

FIGS. 9A-9C illustrate perspective, side, and sectional views of another embodiment of the technology.

DETAILED DESCRIPTION

Various embodiments are described more fully below with reference to the accompanying drawings, which form a part hereof, and which show specific exemplary embodiments for practicing the technology. However, embodiments may be implemented in many different forms and should not be construed as limited to the embodiments set forth herein; rather, these embodiments are provided so that this disclosure will be thorough and complete, and will fully convey the scope of the technology to those skilled in the art. Embodiments may be practiced as methods, systems or devices. The following detailed description is, therefore, not to be taken in a limiting sense. For example, although embodiments of the present technology are useful in severing septa for treating cellulite and fragmenting adipose tissue as part of a UAL procedure, the present technology is not limited thereto. Embodiments of the present technology can be used to cut or fragment other types of tissue.

Figure 1:
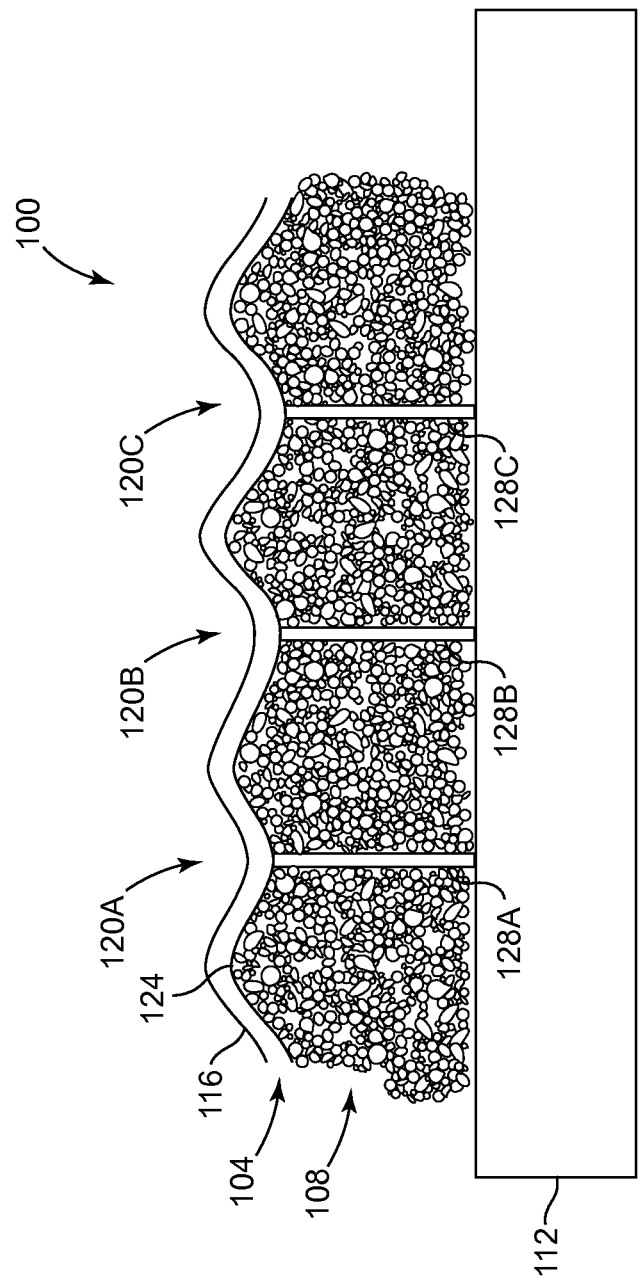
FIG. 1 illustrates a cross-section of tissue that has cellulite.

FIG. 1 illustrates a cross-section of a portion of animal tissue 100. Tissue 100 includes a skin layer 104, a layer of fat 108, and an underlying anatomical layer 112, e.g., a muscle layer. Fibrous tissue, in the form of septa 128A-C, attaches the skin layer 104 to the underlying anatomical layer 112.

An outer surface 116 of skin layer 104 is affected by cellulite. The cellulite manifests itself as a number of dimples on outer surface 116, e.g., dimples 120 A-C. As is illustrated in FIG. 1, the dimples 120A-C result from fat cells within layer 108 pushing up against an inside surface 124 of skin layer 104. As the fat cells push up against inside surface 124, those portions of skin layer 104 where the septa 128A-C connect to the inside surface of skin layer 104, do not stretch or bulge out as much as the other portions, which results in the dimples 120A-C on the outer surface 116.

Figure 2A:
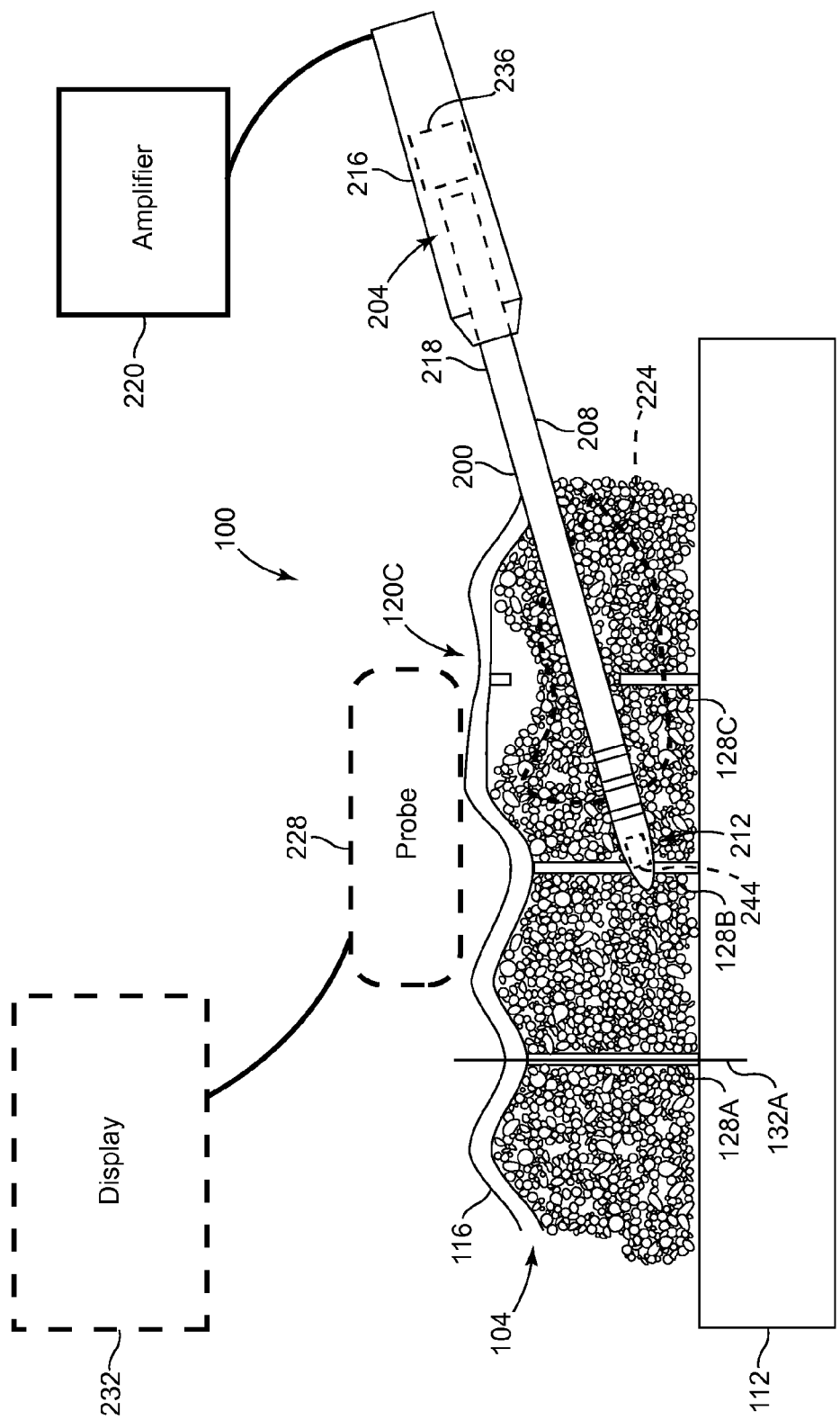
FIG. 2A illustrates the cross-section of tissue shown in FIG. 1, showing treatment of the tissue with an ultrasonic probe according to one embodiment of the present technology and showing a portion of the tissue after such treatment.

FIG. 2A illustrates the cross-section of tissue 100 shown in FIG. 1, with a portion of tissue 100 in the process of being treated and a portion of tissue having been treated already with an ultrasonic probe 200 according to one embodiment of the present technology. Ultrasonic probe 200 includes a proximate end 204 that is configured to connect to an ultrasonic driver assembly (not shown). Ultrasonic probe 200 also includes a shaft 208 that connects the proximate end 204 to a distal end 212. In embodiments, probe 200 has a diameter of about 2 mm to about 10 mm, such as between about 3 mm to about 4 mm. It is in embodiments between about 10 cm to about 30 cm in length, such as between about 15 cm to about 25 cm in length.

In embodiments, the proximate end 204 is connected to an ultrasonic driver assembly that is positioned within a handpiece 216 as shown in FIG. 2A. The ultrasonic probe 200 is manipulated by a surgeon using handpiece 216. The ultrasonic driver assembly within handpiece 216 is connected to amplifier 220 which drives the ultrasonic driver assembly. The ultrasonic driver assembly generates ultrasonic energy that is transmitted from the proximate end 204 through shaft 208 to distal end 212 where it is applied to a surgical site within tissue 100. Amplifier 220, in embodiments, provides a pulsed signal for driving the ultrasonic driver assembly. In one embodiment, the signal is the same or similar to one or more of the pulsed signals shown and described in U.S. Pat. No. 6,391,042, entitled PULSED ULTRASONIC DEVICE AND METHOD, which is hereby incorporated by reference herein in its entirety as if set forth herein in full. In other embodiments, the amplifier is capable of providing signals with characteristics (e.g., frequencies) that are optimized for cutting fibrous tissue and different signals that are optimized for fragmenting and emulsifying adipose tissues. A surgeon can change settings on amplifier 220 to change the signal so that it is optimized for the tissue being treated. In embodiments, handpiece 216 and amplifier 220 are part of the VASER® ultrasound system available from Sound Surgical Technologies LLC, of Louisville, Colo.

The distal end 212 of probe 200 includes a notch 244 with a cutting surface that is used to sever fibrous tissue such as septa 128A-C. Embodiments of notch 244 are shown in more detail in FIGS. 3B and 3C below.

FIG. 3A illustrates probe 200 and its central axis 240. Notch 244 is formed by creating a recess on tip 248 of distal end 212. FIG. 3B illustrates a front view of distal end 212 showing notch 244 from the direction illustrated by arrow 252. FIG. 3C illustrates a top view of probe 200 showing notch 244 from the direction illustrated by arrow 256.

As shown in FIGS. 3B and 3C, notch 244 has a length L and a width W which are substantially perpendicular to central axis 240, and a depth D that is substantially parallel to central axis 240. Notch 244 includes side walls 260A and 260B. In the embodiment shown in FIGS. 3B and 3C, sidewalls 260A and 260B are tapered from bottom 268 to outer surface 264 of tip 248. It is noted that although sidewalls 260A and 260B are shown as tapered, in other embodiments they are straight. Notch 244 also includes surfaces 272A and 272B, which taper from an outer surface 276 of probe 200 to a bottom 268 creating a sharpened edge at bottom 268.

In embodiments, notch 244 has a length (L) and width (W) of between about 2 mm to about 10 mm, such as between about 3 mm to about 4 mm, depending on the dimensions of the ultrasonic probe 200. The notch may have a depth (D) of between about 0.25 mm to about 5 mm.

Referring back to FIG. 2A, septa 128C has been severed using the notch 244 on the distal end 212 of ultrasonic probe 200. The combination of the cutting surface at bottom 268 and the ultrasonic energy allows ultrasonic probe 200 to easily sever the septa 128C without requiring the surgeon to apply very much force. A surgeon can therefore quickly and easily sever septa 128A-C without fear of applying force that accidentally thrusts probe 200 into undesirable areas of tissue 100. While not intending to be bound by any theory of operation, it is presently believed that the relatively sharp edges on the notch enhance the ability to cut fibrous tissue when the fibrous tissue and notch are physically engaged and ultrasonic energy is applied.

As can be appreciated, in order to position fibrous tissue within notch 244, notch 244 must be oriented properly, namely with sidewalls 260A and 260B parallel to a long axis of the fibrous tissue. In the embodiment shown in FIG. 2A, sidewalls 260A and 260B are substantially parallel to a long axis 132A of septa 128A. To maintain this orientation, an orienting feature 218 is provided, in some embodiments, on probe 200. In embodiments, orienting feature 218 is a line or other indication that allows a surgeon to know the orientation of notch 244. Orienting feature 218 may be printed or scribed on probe 200.

As a result of having severed septa 128C, dimple 120C is less pronounced. A surgeon can then follow up with additional treatment, such as removal, or movement, of adipose tissue under dimple 120C to further smooth out dimple 120C. As noted below, in some embodiments probe 200 may also be used to fragment and emulsify tissue in layer 108, before, during, or after severing of septa. As can be appreciated, using ultrasonic probe 200, a surgeon can quickly and easily treat the cellulite on the outer surface 116 of skin layer 104 by severing all of septa 128A-C and smoothing out dimples 120A-C.

In addition to severing septa 128C, the distal end 212 of ultrasonic probe 200, in some embodiments, is also used to fragment and emulsify adipose tissue. As illustrated in FIG. 2A, a volume of adipose tissue 224 has been emulsified by ultrasonic probe 200. As can be appreciated, in embodiments, prior to inserting ultrasonic probe 200 into tissue 100, there is a step of infiltrating tissue 100 with infiltration solution that aids in fragmentation and emulsification of the adipose tissue and contains a local anesthetic to numb tissue 100. After fragmentation and emulsification, the volume of adipose tissue 224 can be aspirated in a separate step with a cannula. Accordingly, probe 200 allows a surgeon to both sever septa and emulsify tissue in a single step. The result is an efficient process that is effective at treating cellulite.

In some embodiments, probe 200 may be a cannula that is also used to aspirate the emulsified adipose tissue 224. In these embodiments, a single instrument (the cannula) can be used to infiltrate tissue 100 with infiltration solution, fragment and emulsify volume 224 of adipose tissue, sever septa 128A-C, and aspirate the volume 224. It is noted that in these embodiments, an aspiration and infiltration system is used to deliver infiltration solution to tissue 102 and remove emulsified tissue 224.

In some embodiments, imaging is used in combination with probe 200 to perform procedures such as treating cellulite. For example, as shown in FIG. 2A, a probe 228, connected to display 232, is positioned on the outside surface 116 of skin layer 104. The probe images tissue 100 and displays the image on display 232 for a surgeon to view. Probe 228 is in embodiments an ultrasound probe with an ultrasonic transducer.

A surgeon uses the image of tissue 100, displayed on display 232, to identify the location of probe 200 within tissue 100, as well as to identify structures such as septa 128A-C. Use of probe 228 and display 232 can improve the efficiency of procedures for treating cellulite performed with probe 200. In some embodiments, probe 228 is hand worn and includes features described in U.S. patent application Ser. No. 12/718,618, entitled THERAPEUTIC PROCEDURE WITH HAND WORN ULTRASOUND TRANSDUCER, which is hereby incorporated by reference in its entirety as if set forth herein in full. In other embodiments, probe 228 is the TouchView® finger probe and is used in combination with the Terason 2000+™ ultrasound system, each available from Sound Surgical Technologies LLC, of Louisville, Colo.

In some embodiments, a pressure sensitive switch 236 is connected to probe 200. Switch 236 is used to control the power delivered to the ultrasonic driver assembly within handpiece 216. Only when a certain amount of pressure is applied to the pressure sensitive switch 236, does the switch 236 turn on and allow the ultrasonic driver assembly to be powered and generate ultrasonic energy. Thus, a surgeon can position fibrous tissue within notch 244 and push probe 200 forward. In response to the force applied by the surgeon, pressure sensitive switch 236 is turned on and power is provided to the ultrasonic driver assembly, which generates ultrasonic energy that is used to sever the fibrous tissue within notch 244. Once the fibrous tissue has been severed, the pressure will be released and switch 236 will be turned off eliminating power to the ultrasonic driver assembly. With pressure sensitive switch 236, ultrasonic energy is only provided to the distal end 212 of probe 200 when there is fibrous tissue within the notch 244 and the surgeon is ready to sever the fibrous tissue. In embodiments, pressure sensitive switch 236 is a miniature snap-action switch, known commonly as a micro switch.

In a method of serving fibrous tissue, the distal end 212 of probe 200 is positioned within at a surgical site within a patient. Fibrous tissue, such as septa 128-A-C, is positioned within notch 244 at the distal end 212 of the ultrasonic probe 200. Ultrasonic energy is then delivered to the distal end of the ultrasonic probe to sever the fibrous tissue within the notch 244. In some embodiments, the method may further include maintaining the delivery of ultrasonic energy to the distal end 212 of the ultrasonic probe 200 to fragment and emulsify adipose tissue at the surgical site. The step of fragmenting and emulsifying adipose tissue may be preceded by an infiltration step in which infiltration fluid is delivered to the surgical site.

Figure 2B:
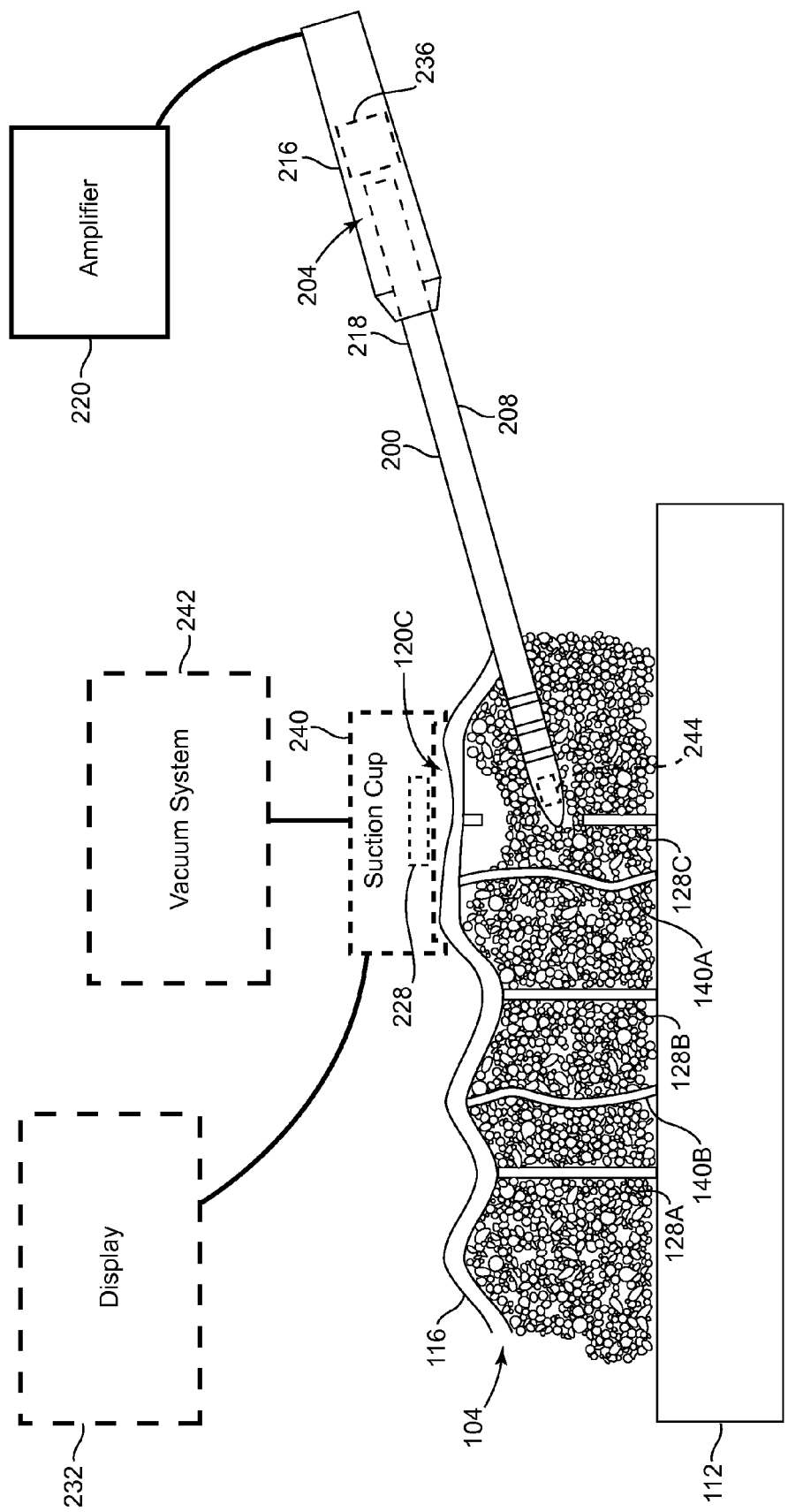
FIG. 2B illustrates a cross-section of tissue with selective severing of septa according to an embodiment of the present technology.

FIG. 2B illustrates another embodiment of the present technology, in which the ultrasonic probe 200 is used to selectively severe some septa, while allowing other septa to remain intact. In some situations, a surgeon may not want to sever all of the septa which connect skin layer 104 to anatomical layer 112. Severing all of the septa may result in the skin layer 104 sliding relative to the anatomical layer. There are some areas of the body, e.g., the buttocks, in which allowing the skin layer 104 to slide with respect to the anatomical layer 112 is not desirable. In these situations, the surgeon will sever only some septa but not other. In one embodiment, septa that are taut and are creating the cellulite are cut, while leaving other septa (e.g., 140A-B) intact to keep the skin layer 104 attached to the anatomical layer 112. As shown in FIG. 2B, septa 140A and 140B have some slack and are not responsible for creating the cellulite on outside surface 116. Septa 140A and 140B are therefore in some embodiments left uncut by a surgeon. A surgeon may use any suitable method or device to identify which septa should be severed and which should remain intact. In one embodiment, as described below, a vacuum system is used to assist a surgeon in identifying the septa that should be severed.

FIG. 2B illustrates use of a vacuum system 242 in combination with the probe 200 for selectively severing septa to treat cellulite. As shown in FIG. 2B, a suction cup 240 is connected to vacuum system 242. Vacuum system 242 creates suction within vacuum cup 240, so that when suction cup 240 is positioned on outside surface 116 it pulls skin layer 104 away from anatomical layer 112. Pulling skin layer 104 away from anatomical layer 112 allows a surgeon to more easily determine which septa are taut and are creating the cellulite. It is noted that although FIG. 2B illustrates a suction cup 240, other embodiments of the present technology may utilize suction pads, suction mats, or other devices that allow skin layer 104 to be pulled away from anatomical layer 112. As shown in FIG. 2B, a surgeon has determined that septa 128C should be severed and has cut it using probe 200. Septa 140A and 140B are not taut and include some slack. A surgeon may therefore decide that these septa should be left intact.

It is noted that although FIG. 2B illustrates a suction cup 240, other embodiments of the present technology may utilize suction pads, suction mats, or other devices that allow skin layer 104 to be temporarily pulled away from anatomical layer 112. As shown in FIG. 2B, a surgeon has determined that septa 128C should be severed and has cut it using probe 200. As a result of having severed septa 128C, dimple 120C is less pronounced than before, (see FIG. I). A surgeon can follow up with additional treatment, such as removal, or movement, of adipose tissue under dimple 120C to further smooth out dimple 120C. Septa 140A and 140B are not taut and include some slack. A surgeon may therefore decide that these septa should be left uncut.

In some embodiments, the suction cup 240 may include the probe 228 used to image tissue. In these embodiments, when tissue is pulled into suction cup 240 it comes in contact with a portion of probe 228 which generates an image of the tissue that is displayed on display 332. In some embodiments, the image generated by probe 228 and displayed on display 232, assists the surgeon in determining which septa should be severed and which should be left intact. The image may show features of the septa, e.g., whether they are taut or have slack, that a surgeon uses to decide whether to sever the septa.

Any appropriate suction cup, suction device, or vacuum system may be used as suction cup 240 and vacuum system 242. Some embodiments of the present technology utilize systems known as MEDCONTOUR™, and MC1™, all of which are distributed by Sound Surgical Technologies LLC, of Louisville, Colo. Other embodiments may utilize different suction devices or vacuum systems.

In some embodiments, the pressure sensitive switch 236 is configured to assist the surgeon in determining which septa should be severed. As noted above, pressure sensitive switch 236 is configured to control the power delivered to the ultrasonic driver assembly within handpiece 216. Only when a certain amount of pressure is applied to the pressure sensitive switch 236, does the pressure sensitive switch 236 turn on and allow the ultrasonic driver assembly to be powered and generate ultrasonic energy. Pressure sensitive switch 236 can be configured so that when a taut septa is positioned within notch 244 by a surgeon, and the surgeon pushes probe 200 forward, the pressure sensitive switch 236 is turned on to allow power to be delivered to the ultrasonic driver assembly. If the septa positioned within the notch 244 have slack, i.e. is not taut, the pressure sensitive switch 236 will not be turned on when a surgeon pushes probe 200 forward; instead the septa will move because of the slack. The pressure sensitive switch 236, in these embodiments, assists the surgeon in distinguishing between septa that are taut and should be cut and septa that are not taut and can be left uncut. As shown in FIG. 2B, the pressure sensitive switch 236 can be used, in some embodiments, in combination with the suction cup 240 and the vacuum system 242.

FIG. 4A illustrates a top view of a distal end 300 of an ultrasonic probe 302, consistent with a first embodiment of the present technology. FIG. 4B illustrates a side view of the embodiment shown in FIG. 4A. As shown in FIG. 4A, distal end 300 includes a notch 304. Within notch 304, is cutting surface 308. When fibrous tissue is positioned within notch 304 it contacts cutting surface 308. The notch 304 helps ensure that fibrous tissue stays in contact with cutting surface 308. Ultrasonic energy transmitted to distal end 300 vibrates cutting surface 308 and aids in severing the fibrous tissue. As described above, the fibrous tissue can be septa, such as septa 128A-C shown in FIGS. 1 and 2.

In addition to notch 304 and cutting surface 308, the embodiment shown in FIGS. 4A and 4B include grooves 312 near distal portion 300. Grooves 312 substantially circumscribe the shaft of probe 302 and function to reduce the tissue contact surface area along and about the sides of the distal end 300 of the shaft of probe 302. The grooves 312 also provide additional tissue fragmenting surface area near the distal end. U.S. Pat. No. 6,360,299, entitled ULTRASONIC PROBE AND METHOD FOR IMPROVED FRAGMENTATION, describes grooves for use in ultrasonic probes. In embodiments of the present technology, grooves 312 incorporate features described in U.S. Pat. No. 6,360,299, which is hereby incorporated by reference herein in its entirety as if set forth herein in full. It is noted that the grooves are optional features that some embodiments of the present technology do not include.

FIG. 4B illustrates a side view of the embodiment shown in FIG. 4A. The distal end 300 of ultrasonic probe 302 is generally blunt or bullet-nosed with smooth and rounded edges with the exception of the portion of distal end 300 that includes the notch 304. In other embodiments, the distal end 300 has sharper edges instead of the rounded edges shown in FIG. 4B.

As described herein, the notch is located at the distal end of the probe. "At the distal end" means at the apex on the end of a probe with a curved tip or on the end surface of a probe with a more blunt tip. It also includes notches that are slightly offset from center on the curved portion of a probe with a curved tip. This is distinguished from the grooves on a probe which extend laterally on the shaft of the probe "near the distal end" of the probe but not "at the distal end" of the probe. These lateral grooves are used for fragmentation. They are not suitable for cutting fibrous tissues, such as septa, since it is difficult to align such a lateral groove with the septa. Further, the lateral grooves are typically not sharp, nor do they create a sharp blade surface necessary for cutting fibrous tissue. In contrast, it is much easier to align the notch at the end of the probe with the septa using techniques such as those mentioned herein. Once the notch and septa are engaged, the physician can gently apply pressure along the axis of the probe to facilitate the transfer of ultrasonic energy via the notch and cutting surface to cut the septa. A notch located "at the end" of the probe can be offset slightly so long as these principles of operation can be achieved.

FIG. 5A illustrates a top view of a distal end 400 of a second ultrasonic probe 402 consistent with another embodiment of the present technology. FIG. 5B illustrates a side view of the embodiment shown in FIG. 5A. Similar to probe 302, probe 402 includes a notch 404 at its distal end 400. Within notch 404, is cutting surface 408. Cutting surface 408 is used to sever fibrous tissue positioned within notch 404. Ultrasonic energy transmitted to distal end 400 vibrates cutting surface 408 and aids in severing the fibrous tissue. Probe 402 also includes grooves 412, which in embodiments are similar to grooves 312.

FIG. 5B illustrates differences between the distal end 300 of ultrasonic probe 302 and the distal end 400 of ultrasonic probe 402. Instead of the blunt, bullet-nosed shape of distal end 300, distal end 400 has a tapered shape. That is, when viewing distal end 400 from the side, thickness D1 is greater than thickness D2, as shown in FIG. 5B.

Figure 6A:
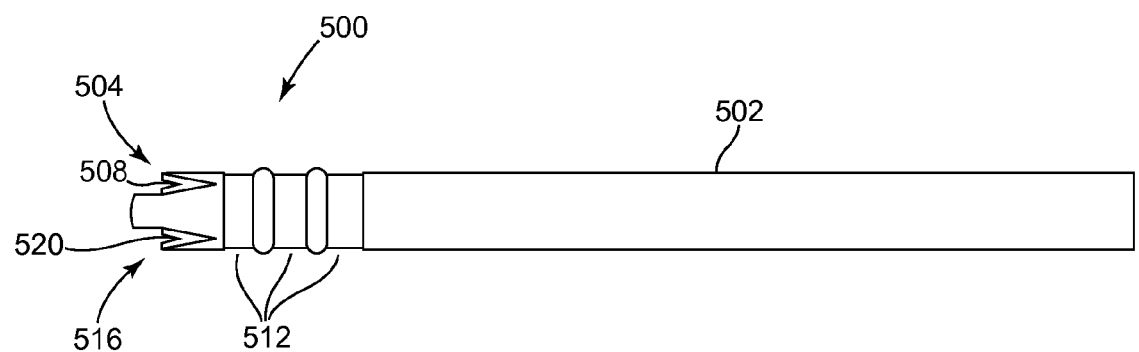
FIG. 6A illustrates a top view of a distal end of an ultrasonic probe consistent with a third embodiment of the present technology.
Figure 6B:
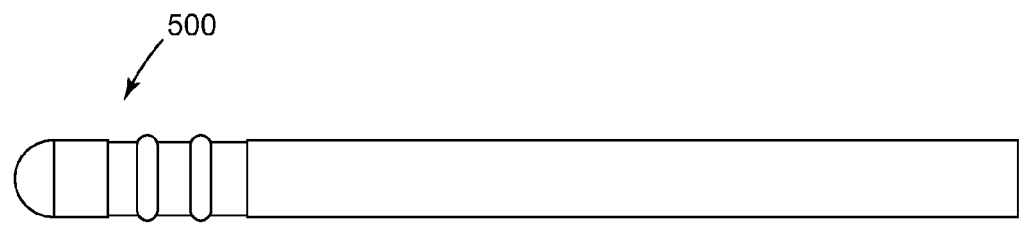
FIG. 6B illustrates a side view of the embodiment shown in FIG. 6A.

FIG. 6A illustrates a top view of a distal end of a third ultrasonic probe consistent with yet another embodiment of the present technology. FIG. 6B illustrates a side view of the embodiment shown in FIG. 6A. As shown in FIG. 6A, distal end 500 includes two notches 504 and 516. Within notch 504 is cutting surface 508, and within notch 516 is cutting surface 520. When fibrous tissue is positioned within either notch 504 or 516 it contacts a cutting surface (508 or 520). Ultrasonic energy transmitted to distal end 500 cutting surfaces 508 and 520 and aids in severing the fibrous tissue. Having two notches makes it more likely for the fibrous tissues to be positioned within a notch for severing. Probe 502 also includes grooves 512, which in embodiments are similar to grooves 312.

As shown in FIG. 6B, the distal end 500 of ultrasonic probe 502 is generally blunt or bullet-nosed with smooth and rounded edges similar to distal end 300. In other embodiments, the distal end 500 has sharper edges instead of the rounded edges shown in FIG. 6B.

Figure 7B:
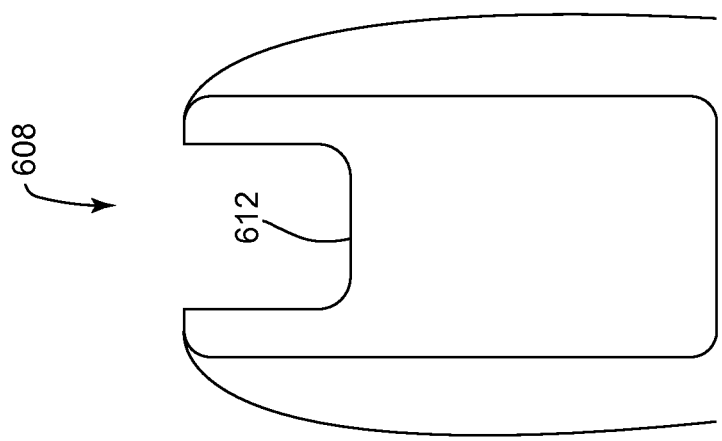
FIGS. 7A and 7B illustrate different notch designs and cutting surface shapes that may be used in ultrasonic probes consistent with embodiments of the present technology.
Figure 7A:
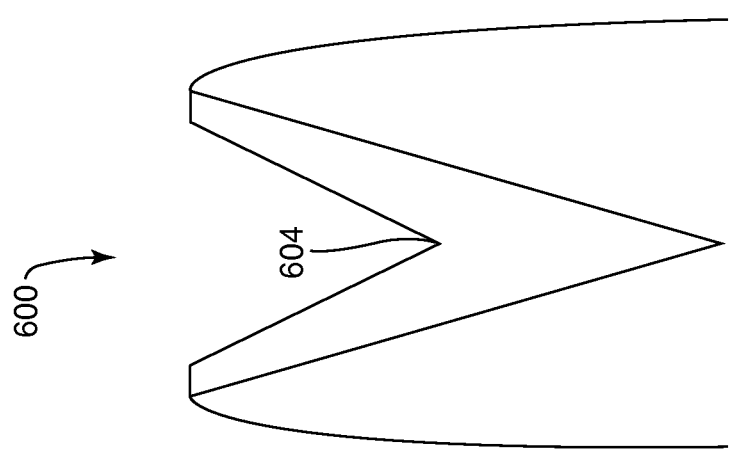

FIGS. 7A and 7B illustrate different notch designs and cutting surface shapes that may be used in embodiments of the present technology. FIG. 7A illustrates a V shaped notch 600 with a cutting surface 604. Notch 600 is similar to notches 308, 408, 508, and 516. FIG. 7B shows a U shaped notch 608 that includes a cutting surface 612. As can be appreciated, cutting surface 612 has a longer edge that may be useful in embodiments for cutting thicker fibrous tissue. FIGS. 7A and 7B are non-limiting examples of different channel and cutting surface shapes that may be used with embodiments of the present technology. Any notch shape and cutting surface shape may be used and still be within the scope of the present technology.

Figure 8:
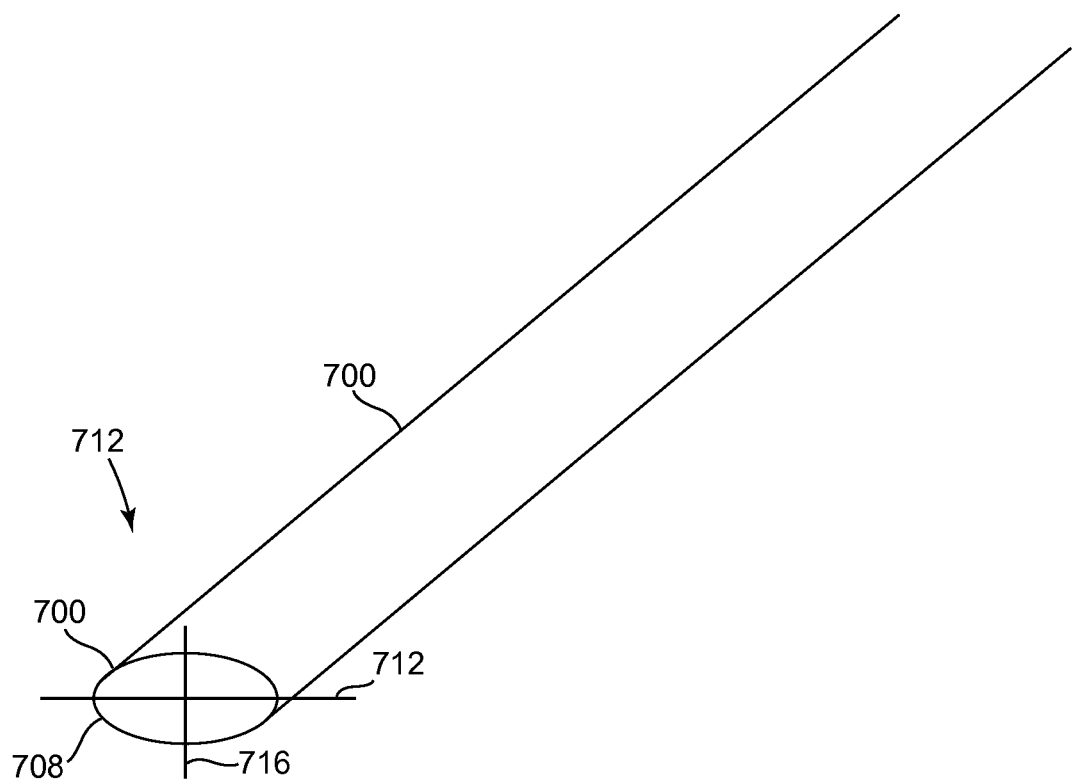
FIG. 8 illustrates a probe with an elliptical cross section consistent with an embodiment of the present technology.

FIG. 8 illustrates another embodiment of a probe 700 that has an elliptical, or in other embodiments a rounded rectangular, cross section 704. Although not shown, probe 700 would also include a notch, at the tip 708 of distal end 712, for severing fibrous tissue. One feature of probe 700 is that the orientation of the notch is easier to determine because the notch features can be oriented in relation to the major axis 712 and the minor axis 716 of cross section 704. Additionally, having an elliptical cross section allows the probe to more closely resemble the shape of a linear incision. That is, the major axis 712 of cross section 704 is positioned parallel to the linear incision. This reduces the stress at the incision site reducing friction and stretching of a patient's skin. This, in embodiments, allows a surgeon to avoid the use of skin ports and instead use a sheath around probe 700. U.S. Pat. No. 6,224,565, entitled PROTECTIVE SHEATH & METHOD FOR ULTRASONIC PROBES, which is hereby incorporated by reference herein in its entirety as if set forth herein in full, describes sheaths that may be used around probe 700 in some embodiments of the present technology. In the embodiment of probe 700 shown in FIG. 8, probe 700 does not include grooves such as grooves (312, 412, and 512). Rather, the outer surface of probe 700 is relatively smooth.

Notched probes of the present technology can be employed in a manner similar to the processes currently employed with ultrasonic assisted lipoplasty using, for example, the VASER® system. In general, the treating physician makes an incision in the skin of the patient and inserts the ultrasonic probe. In a preferred embodiment of the present technology, the notched probe is inserted in a position generally horizontal to the skin surface and oriented with the notch perpendicular to the skin. The makes it easier for the physician to align the notch with the septa and to obtain maximum contact of the septa with the notch. Among other things, it avoids the necessity of rotating the probe to achieve alignment of the notch and the septa. When alignment is achieved, the physician can apply gentle pressure along the probe while ultrasonic energy is applied to sever the septa easily. One or more septa can be severed in this manner. Before, during, or after the severing process ultrasonic energy can also be applied to the probe to emulsify adjacent fat tissue. The fat tissue can then be extracted by the application of suction as known in the art.

Figure 9B:
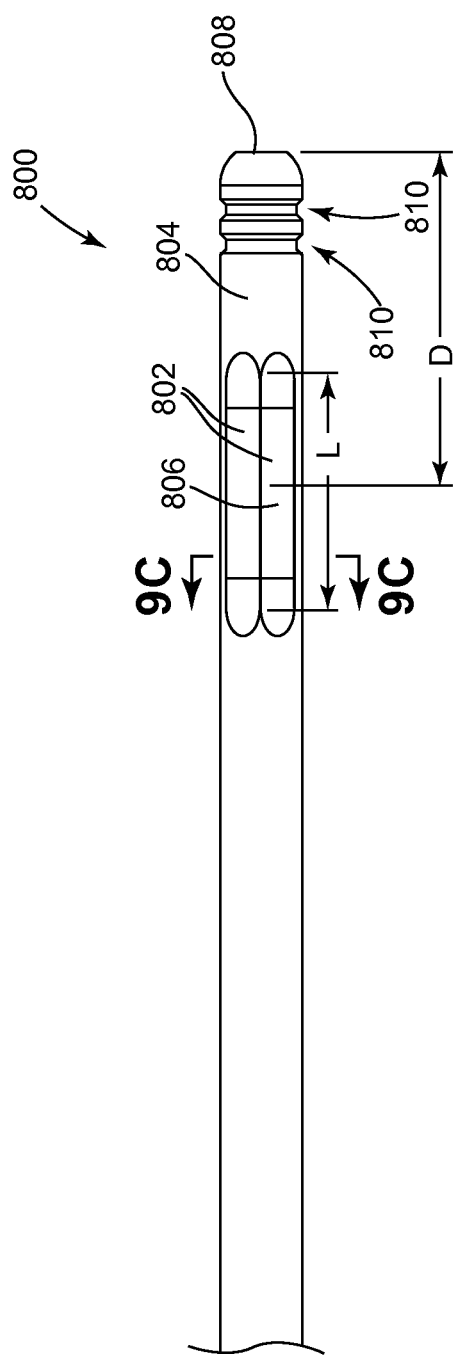
Figure 9C:
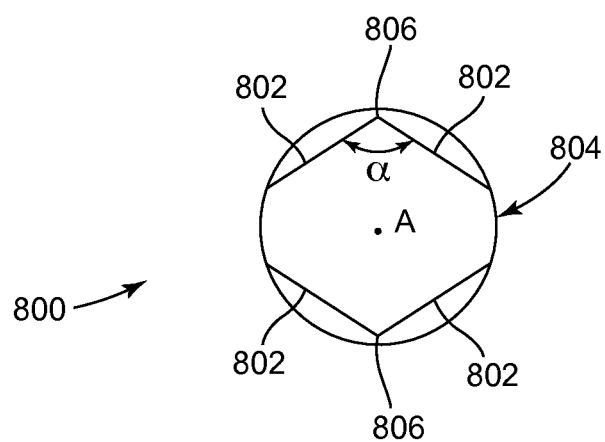

FIGS. 9A-9C depict another embodiment of the probe 800. Here, cutting surfaces 802 are formed along an outer surface 804 of the ultrasonic probe 800. This provides for a longer cutting edge 806, which reduces the need to precisely position the end of the probe 800 on the septa, as is needed with the embodiments previously described. The cutting surfaces 802 join at the edge 806, which performs the cutting action when the ultrasound amplifier is activated. These cutting surfaces 802 are formed symmetrically about the probe axis A, so as to not introduce dynamic asymmetries into the probe 800. Such asymmetries can cause unwanted lateral vibration of the probe 800, leading to premature mechanical failure. When using this embodiment, the surgeon places the probe 800 alongside the septa to be cut, and then energizes the ultrasound amplifier and transducer, and moves the end of the probe 800 in a lateral motion, much like a scalpel. Grooves 810 may also be used to dissolve fat, a described above.

As can be seen in FIG. 9C, removal of probe material to form the cutting surfaces 802 reduces the cross-sectional area of the probe 800. It has been discovered that removal of probe material so as to reduce the cross-sectional area by no more than about 20% is desirable to maintain an acceptable operational life of the probe 800. That is, if too much of the cross-sectional area is removed to form the cutting surfaces 802, the ultrasonic waves may cause more rapid degeneration of the probe material, leading to premature failure. Accordingly, while it may be desirable to form a fairly acute angle α between adjacent cutting surfaces 802, too acute of an angle α will remove too much cross-sectional material, leading to undesirable failure. It is expected that reduction in cross-sectional area by about 5% to up about 20% may produce a probe displaying acceptable longevity while still producing adequate cutting functionality. That is, the cross-sectional area of the portion of the probe bounded by the cutting surfaces 802 and the outer surface 804 (i.e., the cutting area cross section) may be between about 80% and about 95% of the cross-sectional area of the portion of the probe bounded only by the outer surface 804 (i.e., the probe body cross section). A cutting area cross-sectional area of about 80% of the probe body cross-sectional area has been found to be particularly advantageous. Additionally, a cutting edge 806 length L of about 1 centimeter may be desirable for certain applications, although lengths of longer or shorter than 1 centimeter may also be acceptable. Of course, longer cutting edges 806 produce longer cuts to tissue. It is also desirable to locate the cutting surfaces 802 such that a center point of the cutting edge 806 is a distance D from the distal tip 808. The ultrasonic signal applied to the probe produces a longitudinal vibration pattern along the probe 800. It has been discovered that locating the center point of the edge 806 at the first antinode away from the distal tip 808 produces the most efficient cutting action. This distance D is frequency dependent. For example, at an ultrasonic frequency of about 36 kHz, the distance D is about 1 inch from the tip 808. Other frequencies may be optimized based on other distances D.

The description above has been provided for illustrative purposes. The present technology is not limited to the features described above and may include additional features not mentioned above. For example, in embodiments, ultrasonic probes of the present technology may have different cross sectional shapes when sectioned perpendicular to a long axis of the probe. The embodiments shown in FIGS. 2A-6B generally have round or elliptical (FIG. 7) cross sectional shapes. In other embodiments, however, the cross-sectional shape may be square, rectangular, diamond, star shaped, or other shape.

Reference has been made throughout this specification to "one embodiment" or "an embodiment," meaning that a particular described feature, structure, or characteristic is included in at least one embodiment. Thus, usage of such phrases may refer to more than just one embodiment. Furthermore, the described features, structures, or characteristics may be combined in any suitable manner in one or more embodiments.

The description above, in some instances, describe embodiments of the present technology as useful for cutting septa to treat cellulite. It is noted that the present technology is not limited to treating cellulite or other specific cosmetic surgery procedures.

One skilled in the relevant art may recognize, however, that the technology may be practiced without one or more of the specific details, or with other methods, structures, materials, etc. In other instances, well known structures or operations have not been shown or described in detail merely to avoid obscuring aspects of the technology.

While example embodiments and applications have been illustrated and described, it is to be understood that the technology is not limited to the precise configuration and resources described above. Various modifications, changes, and variations apparent to those skilled in the art may be made in the arrangement, operation, and details of the methods and systems disclosed herein without departing from the scope of the claimed technology.

I claim:

1. An ultrasonic probe for conducting ultrasonic energy to a surgical site for use in severing fibrous tissue and fragmenting adipose tissue, the ultrasonic probe comprising:
    a shaft including a distal end and a proximate end configured to connect to an ultrasonic driver assembly that generates the ultrasonic energy, the shaft configured to conduct the ultrasonic energy from the proximate end to the distal end; and
    a first cutting surface located proximate the distal end of the shaft,
    wherein the first cutting surface is configured to contact and sever the fibrous tissue, and the first cutting surface has a center point located at a distance from the distal end of the ultrasonic probe that corresponds to an antinode of an ultrasonic longitudinal vibration pattern produced by the delivery of ultrasonic energy to the distal end of the shaft.

2. The ultrasonic probe of claim 1, wherein the shaft comprises an outer surface, wherein the outer surface at least partially defines the cutting surface.

3. The ultrasonic probe of claim 2, wherein the outer surface defines a substantially rounded profile and the cutting surface defines a substantially flat profile.

4. The ultrasonic probe of claim 2, further comprising:
    a second cutting surface located symmetrically on the outer surface relative to the first cutting surface.

5. The ultrasonic probe of claim 1, further comprising:
    one or more grooves near the distal end,
    wherein the one or more grooves are located between the distal end of the shaft and the first cutting surface.

6. An ultrasonic probe for conducting ultrasonic energy to a surgical site for use in severing fibrous tissue and fragmenting adipose tissue, the ultrasonic probe comprising:
    a probe body including a tip, a plurality of cutting edges proximate to the tip, an outer surface, and a plurality of grooves extending circumferentially about the outer surface proximate to the tip,
    wherein the grooves are located between the tip and the cutting edges along a longitudinal axis of the probe body, and the cutting edges are oriented parallel to the longitudinal axis of the probe body.

7. The ultrasonic probe of claim 6, wherein the probe body has a cross-sectional area, and the portion of the probe body including the cutting edges has a cross-sectional area that is about 95% to about 80% of the cross-sectional area of the probe body.

* * * * *